(12) United States Patent
Bourhy et al.

(10) Patent No.: US 9,714,944 B2
(45) Date of Patent: Jul. 25, 2017

(54) **USE OF *LEPTOSPIRA FAINEI* SEROVAR HURSTBRIDGE BACTERIA FOR DIAGNOSING *LEPTOSPIROSIS***

(71) Applicant: INSTITUT PASTEUR, Paris (FR)

(72) Inventors: Pascale Bourhy, Chaville (FR); Suzanne Chanteau, Tahiti (PF); Cyrille Goarant, Noumea (PF); Mathieu Picardeau, Paris (FR); Faradibano Nato, Antony (FR); Sylvie Dartevelle, Neauphle-le-chateau (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 14/433,030

(22) PCT Filed: Oct. 4, 2013

(86) PCT No.: PCT/EP2013/070664
§ 371 (c)(1),
(2) Date: Apr. 1, 2015

(87) PCT Pub. No.: WO2014/053615
PCT Pub. Date: Apr. 10, 2014

(65) Prior Publication Data
US 2015/0253325 A1   Sep. 10, 2015

(30) Foreign Application Priority Data
Oct. 4, 2012 (EP) .................... 12306215

(51) Int. Cl.
*A61K 39/02* (2006.01)
*G01N 33/569* (2006.01)
*G01N 33/554* (2006.01)

(52) U.S. Cl.
CPC ..... *G01N 33/56911* (2013.01); *G01N 33/554* (2013.01); *G01N 2333/20* (2013.01); *G01N 2469/20* (2013.01)

(58) Field of Classification Search
None
See application file for complete search history.

(56) References Cited

FOREIGN PATENT DOCUMENTS

| WO | 98/40099 | 9/1998 |
|---|---|---|
| WO | 2008/108510 A1 | 9/2008 |
| WO | 2009/004056 A1 | 1/2009 |

OTHER PUBLICATIONS

Colleen Lau, et al., "Leptospirosis: An emerging disease in travellers, " Travel Medicine and Infectious Disease (2010) 8, 33-39.
Alan J.A. McBride, et al., "Leptospirosis," Curr Opin Infect Dis (2005) 18:376-386.

Yupin Suputtamongkol, et. al., "Strategies for Diagnosis and Treatment of Suspected Leptospirosis: A Cost-Benefit Analysis," PLoS Negl Trop Dis 4(2): e610.
C. Goarant, et al., "Outbreak of leptospirosis in New Caledonia: diagnosis issues and burden of disease," Tropical Medicine and International Health, vol. 14 No. 8 pp. 926-929 Aug. 2009.
R. A. Hartskeerl, "Emergence, control and re-emerging leptospirosis: dynamics of infection in the changing world," Clin Microbiol Infect 2011; 17:494-501.
P. Perolat "*Leptospira fainei* sp. nov., isolated from pigs in Australia," International Journal o f Systematic Bacteriology (1998), 48, 851-858.
R. J. Chappel, et al., "Serological titres to Leptospira fainei serovar hurstbridge in human sera in Australia," Epidemiol. Infect. (1998). 121, 473-475.
Wiepko J. Terpstra, et al., "Serodiagnosis ofHuman Leptospirosis by Enzyme-Linked-Immunosorbent-Assay (ELISA)," Zbl. Bakt. Hyg., LAbt. Orig. A 247,400-405 (1980).
Alain Berlioz-Arthaud, et al., "Multicentre survey of incidence and public health impact of leptospirosis in the Western Pacific," Transactions of the Royal Society of Tropical Medicine and Hygiene (2007) 101, 714-721.
Suzanne Chanteau, et al, "New Rapid Diagnostic Tests for Neisseria meningitidis Serogroups A, W135, C, and Y," (2006) New rapid diagnostic tests for Neisseria meningitidis serogroups A, W135, C, and Y. PLoS Med 3(9): e337.
Rosanna W. Peeling, et al., "Evaluation of diagnostic tests: dengue," Nature Reviews Microbiology, 2010, S30-S38.
David L. Simel, et al., "Likelihood Ratios With Confidence: Sample Size Estimation for Diagnostic Test Studies," J. Clin Epidmiol vol. 44, No. 8, pp. 763-770,1991.
Afina S. Glas, et al., "The diagnostic odds ratio: a single indicator of test performance," Journal of Clinical Epidemiology 56 (2003) 1129-1135.
Pascale Bourhy, et al., "Evaluation of an in-house ELISA using the intermediate species Leptospira fainei for diagnosis of leptospirosis," Journal of Medical Microbiology (2013), 62, 822-827.
Cyrille Goarant, et al., "Sensitivity and Specificity of a New Vertical Flow Rapid Diagnostic Test for the Serodiagnosis of Human Leptospirosis," (2013) Sensitivity and Specificity of a New Vertical Flow Rapid Diagnostic Test for the Serodiagnosis of Human Leptospirosis. PLoS Negl Trop Dis 7(6): e2289.
Uraiwan Kositanont, et al., "Detection and differentiation between pathogenic and saprophytic *Leptospira* spp. by multiplex polymerase chain reaction," Diagnostic Microbiology and Infectious Disease 57 (2007) 117-122.
Kanti Laras, et al., "The Importance of Leptospirosis in Southeast Asia," Am. J. Trop. Med. Hyg., 67 (3), 2002, pp. 278-286.
Andreas M. Petersen, et al., "First isolation of Leptospira fainei serovar Hurstbridge from two human patients with Weil's syndrome," J. Med. Microbiol. Ð vol. 50 ?2001), 96-100.

*Primary Examiner* — Jennifer Graser
(74) *Attorney, Agent, or Firm* — Arrigo, Lee & Guttman LLP (57) ABSTRACT

The present invention discloses an in vitro method for diagnosing a *Leptospira* infection in a biological sample of a subject, comprising a step of contacting said sample with bacterial cells of a serovar of the *Leptospira fainei* species, preferably bacterial cells of the *Leptospira fainei* serovar Hurstbridge, or an antigenic fraction of said bacterial cells. In a preferred embodiment, said *Leptospira* infection is not due to bacteria belonging to the serovar of the *Leptospira fainei* species used in the diagnostic method.

8 Claims, 2 Drawing Sheets

USE OF *LEPTOSPIRA FAINEI* SEROVAR HURSTBRIDGE BACTERIA FOR DIAGNOSING *LEPTOSPIROSIS*

BACKGROUND OF THE INVENTION

Outbreaks of leptospirosis are of significant and growing public health concern in many tropical and subtropical countries. Leptospirosis is a zoonotic disease caused by spirochaetes of the genus *Leptospira*, which are classified into 9 pathogenic species and more than 200 serovars on the basis of structural heterogeneity in the carbohydrate component of the lipopolysaccharide. Human infections are endemic in most tropical and most moderate climates. Globally, an estimated number of >500,000 severe cases occur annually with fatality rates exceeding 10%.

This neglected infectious disease is also reported to be an emerging or re-emerging disease in industrialized countries, with probable increasing impacts due to global warming and increasing travel-related cases [Lau C, *Travel Med Infect Dis.* 2010]. The incidence is underestimated due to highly variable clinical presentation which is characterized by non-specific signs and symptoms; leptospirosis is often confused with other diseases such as dengue, rickettsiosis, enteric fevers and malaria. The complete triad of Weil's disease (hepatic failure, renal failure and hemorrhage) is recognized to account for less than one third of human cases [Mac Bride A. J. et al., *Curr. Opin. Infect. Dis.* 2005]. Most of the early signs and symptoms point to the so-called "acute fever of unknown origin" (FUO), a major diagnostic challenge in tropical and subtropical areas. Because of nonspecific symptoms in human leptospirosis, the biological confirmation is needed to ascertain the disease. In many endemic regions, the laboratory diagnosis of leptospirosis is not available due to a lack of reliable, rapid and simple diagnostic assay for a point of care diagnosis of human leptospirosis.

Yet, an early and proper antibiotic treatment is a key determinant of the outcome in leptospirosis [Suputtamongkol Y. et al, *PLoSNegl. Trop. Dis.* 2010], because, in contrast to many similar diseases (e.g. dengue), leptospirosis can easily be treated with antibiotics in its early stages. However, the diagnosis has to be confirmed before the 5th day after disease onset, when treatment with antibiotics is most effective.

The need for reliable Rapid Diagnostic Tests (RDTs) for diagnosing human leptospirosis has therefore been largely recognized. Preferably, these RDTs should be portable, so that they can be used directly on the bedside, even in remote health centers, so as to improve clinical management of leptospirosis patients in remote dispensaries of tropical and subtropical regions.

Currently, the laboratory diagnosis for leptospirosis relies on the detection of antibodies raised against the *Leptospira* bacteria by serological techniques such as Microscopic agglutination test (MAT), or of spirochaete nucleic acids by PCR [Goarant C. *Trop. Med. Int. Health,* 2009). However, these techniques are inappropriate for early clinical care in peripheral health centers that support the major part of the leptospirosis burden, because they are time-consuming and require sophisticated materials that are most frequently available only in central reference laboratories [Hartskeerl R A, *Clin. Microbiol. Infect.* 2011]. Also, serological techniques such as Microscopic agglutination test (MAT) are limited by the fact that they use few representative group of serovar antigens, so that a negative reaction on serial samples does not rule out the possibility that the patient might actually be infected with a *Leptospira* serovar not included in the battery of the tested antigens. PCR-based techniques, although very sensitive and early tests, are technically demanding and the leptospires disappear from the blood vessels approximately at day 7 after infection.

Moreover, ELISA-based assays using crude whole-cell lysates of *Leptospira* strains (usually the saprophyte *L. biflexa* serovar Patoc strain Patoc 1) as antigens may not recognize the diversity of circulating strains and the sensitivity of these tests is generally poor (Mc Bride A J. et al, *Curr. Opinion Infect Dis,* 2005).

Thus, the biological confirmation of leptospirosis is currently not satisfactory, as it is not reliable, tedious and rarely available in a timely manner.

In fact, a major challenge is still to discover antigens that are conserved across the major *Leptospira* strains, since such antigens would potentially be recognized by most of the antibodies generated in *Leptospira*-infected patients.

In this context, the present inventors have identified a *Leptospira* antigen which allows the detection of a broad spectrum of antibodies directed against most of the serovars. This *Leptospira* antigen is expressed by the bacteria of the serovar Hurstbridge, which was originally isolated from pigs in Australia [Perolat P. et al, *Int. J. Syst. Bacteriol.* 1998] and is now classified in the species *Leptospira fainei*, known to also infect humans [Chappel R J. et al, *Epidemiol. Infect.,* 1998]. The present inventors indeed demonstrated that this antigen presents a high reactivity towards antibodies generated by several leptospirosis serogroups, even distantly serologically related, such as serogroups Australis, Autumnalis, Ballum, Bataviae, Canicola, Cynopteri, Grippotyphosa, Hebdomadis, Icterohaemorrhagiae, Panama, Pomona, Pyrogenes, Sejroe and Tarassovi, on serum samples of a number of metropolitan French patients. Of note, false positive results are excluded since the serovar Hurstbridge is poorly represented outside Australia and New Zealand. The present inventors also identified a method to inactivate the bacteria of the serovar Hurstbridge so as to enhance the exposure of said antigen at the bacterial cell surface.

Using such an antigen, it is possible to develop different Rapid Diagnostic Tests (RDTs) exhibiting high sensitivity and specificity for numerous *Leptospira* serovars.

As disclosed below in detail, the present inventors developed two different RDTs, that are i) an ELISA test and ii) a vertical flow immunochromatography dipstick assay, these two RDTs using heat-inactivated *Leptospira fainei* bacteria as antigen, for detecting anti-*Leptospira* human IgM in human serum samples. The robustness of these two RDTs is very satisfactory in terms of sensitivity, specificity, reproducibility, and shelf-life.

It is possible to use the ELISA and dipstick assay of the invention as robust, simple, and rapid diagnostic tools for diagnosing leptospirosis in patients presenting early signs and symptoms thereof.

Moreover, as the dipstick assay of the invention does not require expensive and complex analysis system, it can therefore be used in remote health centers, or in remote dispensaries of tropical and subtropical regions.

As *Leptospira fainei* bacteria presents a high reactivity towards antibodies generated by several leptospirosis serogroups, the present inventors also propose to use *Leptospira fainei* bacteria as antigen in a Microscopic Agglutination Test (MAT).

DETAILED DESCRIPTION OF THE INVENTION

In a first aspect, the present invention discloses an in vitro method for diagnosing a *Leptospira* infection in a biological sample of a subject, comprising a step of contacting said sample with bacterial cells of a serovar of the *Leptospira fainei* species, or an antigenic fraction of said bacterial cells.

In this aspect, the said *Leptospira* infection is not due to bacteria belonging to the said serovar. In other words, when the diagnostic method of the invention uses bacteria of a define serovar of the *Leptospira fainei* species, then this method is not intended to be used for diagnosing an infection mediated by this define serovar.

As used herein, the term "antigen" herein means any molecule (e.g., protein, lipoprotein, polysaccharide, and/or glycoprotein) that causes the immune system to produce antibodies against the said substance. An "immunogenic" antigen is a specific type of antigen which is able to stimulate an adaptive immune response if injected on its own. At the molecular level, an antigen is thus characterized by its ability to be recognized and "bound" by the antigen-binding site of an antibody.

In the context of the present invention, the term "antigenic fraction the invention" designates an antigen which is expressed specifically by bacterial cells of the *Leptospira fainei* species. This antigen is accessible especially when said bacteria have been inactivated with a heating and optionally with a chemical treatment. Importantly, this antigen is expressed by a number of bacteria of other serogroups or serovars. More precisely, the antigenic fraction of the invention corresponds to an antigen i) which is expressed by the bacterial cells of the *Leptospira fainei* species and ii) which is recognized by antibodies that are found in the serum of subjects infected with bacteria belonging to the following serogroups: Australis, Autumnalis, Ballum, Bataviae, Canicola, Cynopteri, Grippotyphosa, Hebdomadis, Icterohaemorrhagiae, Panama, Pomona, Pyrogenes, Sejroe and Tarassovi.

*L. fainei* belongs to the intermediate group of *Leptospira* [Perolat P., *Int. J. Syst. Bacteriol.*, 1998]. Without being bound by the theory, it is hypothesized that this species may share common antigenic features with saprophytes and pathogens which constitute the two other phylogenetic groups in the genus *Leptospira*. This would explain why the antigen of the invention is recognized by several anti-*Leptospira* antibodies, and in particular antibodies generated in subjects which are infected with bacteria that do not belong to the *L. fainei* species.

The antigenic fraction of the invention can be a protein, a lipoprotein, a polysaccharide, and/or a glycoprotein. It is preferably lipopolysaccharide (LPS, which remains intact upon heating of the bacterial cells), a secreted protein, a cytoplasmic protein, or a protein of the cellular membrane of the bacteria of the *Leptospira fainei* serovar Hurstbridge, for example an envelope membrane protein. More preferably, the said antigenic fraction is LPS.

In the context of the present invention, an antigenic fraction (or an antigen) is said to be "recognized", "specifically recognized" or "bound" by an antibody if said antibody has an affinity constant $K_a$ (which is the inverted dissociation constant, i.e. $1/K_d$) higher than $10^5$ $M^{-1}$, preferably higher than $10^6$ $M^{-1}$, more preferably higher than $10^7$ $M^{-1}$ for said antigen (or epitope).

In a preferred embodiment, the diagnosis method of the invention requires the use of bacterial cells (or antigenic fraction thereof) of the *Leptospira fainei* serovar Hurstbridge. In a preferred embodiment, the said bacteria are cells of the strain BUT 6, which were originally isolated from pigs in Australia [Perolat P. et al, *Int. J. Syst. Bacteriol.*, 1998] and are now classified in the species *Leptospira fainei* [Chappel R J. et al, *Epidemiol. Infect.*, 1998]. These bacteria have been referenced as *L. fainei* Hurstbridge 1 and are available in international collections (e.g. ATCC BAA-1109$^T$ or CRBIP6.1209$^T$). The 16S rDNA partial sequence of the prototype strain of *L. fainei* is referenced as GeneBank accession no. U60594, AY631885, AY995712 and FJ154578. The diagnosis method of the invention preferably uses bacterial cells of the *Leptospira fainei* species that have been previously inactivated or killed, preferably by a heating treatment. Some of these treatments are described in Terpstra W J. et al., *Zentralbl Bakteriol A.* 1980.

These particular treatments are referred to hereafter as "inactivating methods" of bacterial cells. They enable to inactivate bacterial cells of the *Leptospira fainei* species so as to induce the appearance of the antigen of the invention, which can then be used in the diagnosis method of the invention.

In one embodiment, whole bacterial cells of the *Leptospira fainei* species are used. These whole bacterial cells are obtained preferably by inactivating them (preferably by heating, as described below), and/or by treating them with conservative agents. These conservative agents are well-known in the art.

In one embodiment, the bacterial cells of the *Leptospira fainei* species are inactivated by means of the so-called "inactivating method of the invention", which comprises at least a step of inactivating the said bacterial cells with a mechanical treatment (e.g., by means of a French Press, sonication, etc.) or a heating treatment (e.g., at a high temperature). This inactivating method of the invention is preferably performed on bacterial cells of the *Leptospira fainei* serovar Hurstridge.

The inactivating method of the invention preferably comprises at least a heating treatment. Thus, the inactivated bacterial cells used in the invention are preferably heat-inactivated. In this heat-based inactivating method, the heating step is typically performed by submitting the live bacterial cells of the *Leptospira fainei* species to high temperature for at least about 10 minutes, preferably for at least about 20 minutes, and more preferably for at least about 30 minutes, and at most for about 1 hour. In order to inactivate efficiently (i.e., at least 90% of the bacterial cells and preferably almost 100% of them) the temperature is preferably comprised between about 60° C. and 150° C., more preferably between about 90° C. and 110° C. and even more preferably around 100° C. This heating treatment can be performed in any system providing a high temperature during the required time (e.g., in an oven, a dry heater, or a boiling bath). Preferably, the heating treatment is performed in a boiling bath. In this case, it is preferable that the cells are kept isolated from the water in a safe recipient.

In another embodiment, the heat- or mechanically-inactivated bacterial cells of the *Leptospira fainei* species are further treated chemically, for example with an inactivating chemical agent.

In this embodiment, said inactivating chemical agent is defined as any chemical agent having preservation and/or antiseptic properties. In particular, preservation of the morphology (shape and structure) of the bacterial cells is important in the context of the invention, as the antigen of the invention may be expressed at the surface of the bacterial cells. Consequently, said inactivating chemical agent is preferably a fixative agent, for example chosen in the group consisting of: aldehyde (such as formaldehyde, glutaraldehyde, and paraformaldehyde), alcohols (such as methanol, ethanol), acetone, oxidizing agents (such as osmium tetroxide, potassium dichromate, chromic acid, and potassium permanganate) and the like. Said inactivating chemical agent is more preferably chosen in the group consisting of: formaldehyde, and paraformaldehyde. The chemical treatment should last sufficiently so that at least 95% of the bacterial cells (and preferably almost 100% of them) are inactivated (in other words, no living bacterial cells should remain in the bacteria sample). The chemical treatment will last typically at least about one hour, and more preferably at least about two hours, and even more than 10 hours, maximally about 24 hours. The duration and the temperature of the reaction obviously depend on the choice of the chemical agent and on its concentration. Since chemical agents which can be used for inactivating bacteria have been known and commercialized for decades, it will be easy for the skilled person to determine the conditions (e.g., duration, temperature, concentration, etc.) to use for inactivating at least 95% of (and preferably all) the bacterial cells with any given chemical agent. For example, as disclosed below, the diagnosis method of the invention requires the use of bacterial cells that have been treated with a 0.2% v/v of formaldehyde (formalin) for two to six hours.

Importantly, the mechanical, the heating or the chemical inactivating treatment can be performed in any order.

However, in a preferred embodiment, the bacterial cells of the *Leptospira fainei* species are first treated chemically with an inactivating chemical agent as defined above, and are secondly heated at a high temperature or mechanically, for example in the conditions defined previously. In a more preferred embodiment, the diagnosis method of the invention requires the use of bacterial cells of the *Leptospira fainei* species that have been first treated with, as an inactivating chemical treatment, 0.2% v/v of formaldehyde (formalin) during two to six hours, and then been heated during 45 minutes in a boiling bath.

As used herein, the term "biological sample" refers to any sample that may contain *Leptospira*-specific antibodies, such as any biological fluid for example serum sample, plasma sample, blood sample, lymph sample, urine sample, or sample of cerebrospinal fluid (CSF). Blood plasma is the liquid component of blood, in which the blood cells are suspended. It is composed of mostly water (90% by volume), and contains dissolved proteins, glucose, clotting factors, mineral ions, hormones and carbon dioxide. It is easily recovered as it corresponds to the supernatant fluid obtained when non-coagulated blood has been centrifuged. To obtain plasma samples, the blood is mixed with an appropriate amount of anticoagulant like heparin, oxalate or ethylene diamine tetra-acetic acid (EDTA), then mixed immediately and thoroughly to avoid clotting. Blood serum corresponds to blood plasma without fibrinogen or the other clotting factors. These proteins are sometimes considered as interfering substances in some tests since they can react with the reagent and thereby yield inaccurate results. Serum is therefore often preferred in clinical testing. Serum samples can be easily obtained by the skilled person by centrifuging blood samples at about 2500 rpm for a few minutes and then recovering the supernatant.

In a preferred embodiment, the diagnosis method of the invention is performed on a biological sample which is a serum sample. Such a serum sample is obtained by a completely harmless blood collection from the subject and thus allows for a non-invasive diagnosis of leptospirosis.

In the context of the present invention, the term "subject" herein designates human or animal individuals.

The method of the invention is usually performed on subjects who are suspected of a leptospirosis. The said subjects usually present at least one symptom known to be associated with such an infection. This symptom is for example fever, chills, myalgia, and/or intense headache.

The method of the invention can also be applied to any individual having suffered from leptospirosis, in order to detect the serotype prevalence of anti-leptospirosis antibodies during or after leptospirosis epidemic event.

In the context of the invention, the expression "diagnosing a *Leptospira* infection" refers to the process of identifying or detecting if a subject or a patient is infected or not with pathogenic bacteria of the genus *Leptospira*. It also refers to the process of monitoring the progression of an infection by said bacteria. In other terms, the method of the invention enables to diagnose a *Leptospira*-induced infection in a subject. It also allows discriminating subjects infected by *Leptospira* bacteria from subjects infected by bacteria from other genus.

It is reminded here that, when the antigen used in the method of the invention is bacterial cells of a defined serovar of the *Leptospira fainei* species, the *Leptospira* infection which is diagnosed according to the method of the invention is not necessarily due to (or caused by) bacteria belonging to the said serovar. In particular, when the antigen used in the method of the invention is bacterial cells of the *Leptospira fainei* serovar Hurstbridge, the *Leptospira* infection which is diagnosed according to the method of the invention is not necessarily due to (or caused by) bacteria belonging to the *Leptospira fainei* serovar Hurstbridge. In a preferred embodiment, the *Leptospira* infection which is diagnosed according to the method of the invention is not due to (or caused by) any bacteria belonging to the *Leptospira fainei* species, and, in particular, to bacteria belonging to the *Leptospira fainei* serovar Hurstbridge. In a more preferred embodiment, the leptospirosis infection which is diagnosed according to the method of the invention is rather due to (or caused by) bacteria belonging to one or more serogroup(s) chosen from Hardjo, Louisiana, Shermani, Celledoni, Sarmin, Javanica, Grippotyphosa, Mini, Serjoe, Australis, Autumnalis, Ballum, Bataviae, Canicola, Cynopteri, Hebdomadis, Icterohaemorrhagiae, Panama, Pomona, Pyrogenes, Sejroe or Tarassovi. In an even more preferred embodiment, the leptospirosis infection which is diagnosed according to the method of the invention is due to (or caused by) bacteria belonging to one or more serogroup(s) chosen from Australis, Autumnalis, Ballum, Bataviae, Canicola, Cynopteri, Grippotyphosa, Hebdomadis, Icterohaemorrhagiae, Panama, Pomona, Pyrogenes, Sejroe and Tarassovi.

As disclosed herein, the term "in vitro" refers to studies or experiments that are conducted using biological samples (e.g. blood or serum samples) which have been isolated from their host organisms (e.g. animals or humans). These experiments can be for example reduced to practice in laboratory materials such as tubes, flasks, wells, microtubes, etc. In contrast, when used herein, the term "in vivo" refers to studies that are conducted on whole living organisms.

An antibody (Ab) is a large Y-shaped protein produced by B-cells that is used by the immune system to identify and neutralize foreign objects such as bacteria and viruses. Native antibodies are usually heterotetrameric glycoproteins of about 150,000 daltons, comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system. Constant regions are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. Of the various human immunoglobulin classes, only human IgG1, IgG2, IgG3 and IgM are known to activate complement; and human IgG1 and IgG3 mediate ADCC more efficiently than IgG2 and IgG4.

Antibodies of IgM and IgG isotypes are composed of two identical heavy chains and two identical light chains joined by disulfide bonds. Importantly, IgM antibodies form polymers where multiple immunoglobulins are covalently linked together through disulfide bonds, mostly as a pentamer but also as a hexamer. In their pentamer form, they have a molecular mass of approximately 900 kDa. Because each monomer has two antigen binding sites, a pentameric IgM has 10 binding sites. IgM antibodies cannot bind 10 antigens at the same time because of steric constraints. Due to its polymeric nature, IgM possesses high avidity.

Of note, IgM antibodies are the first to appear in response to initial exposure to antigen, and the presence of specific IgG, in general, corresponds to maturation of the antibody response.

With the diagnosis assays of the prior art, both IgG and IgM type antibodies were usually detected in the biological sample of the patients. In contrast, however, the dipstick and ELISA assays of the invention are specific to IgM type antibodies induced by the *Leptospira* infection, so that the leptospirosis is diagnosed at an early stage and can therefore be more efficiently cured. In addition, and because IgM titers are known to decline faster than IgG, some positive MAT results may reveal IgGs remaining from previous exposure to leptospires, and could therefore be less specific than IgM-specific assays to detect acute and recent leptospirosis.

The identification of the IgM antibodies is performed by using either polyclonal antibodies, or monoclonal antibodies, or antibody functional fragments, used as "revealing agent". As used herein, "antibody functional fragments" is intended to include Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques. A "monoclonal antibody", as used herein, means an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

Of note, the diagnosis method of the invention can use either live bacterial cells or inactivated bacterial cells.

Live bacterial cells of the *Leptospira fainei* species can be used for example in a MAT assay. Such a MAT assay consists in serial dilutions of the patient's serum kept in contact with an equal volume of a well grown suspension of leptospires and read microscopically by estimating 50% agglutination as the end-point titer of the reaction mixture. This assay is broadly used in the art. Briefly, the bacterial cells are grown in an appropriate medium (typically the dedicated Ellinghausen and Mc Cullough modified Johnson & Harris (EMJH) medium) and put in contact with different dilutions of the tested serum. The agglutination is then observed under a dark field microscope.

Advantageously, although it is performed with bacteria of a defined serovar (for example Hurtsbridge), the MAT assay of the invention enables to diagnose an infection due to bacteria belonging to other serogroups and/or serovars as mentioned above.

In a preferred embodiment, however, the diagnosis method of the invention uses bacterial cells of the *Leptospira fainei* species which have been inactivated according to the "inactivating method" of the invention (as defined above) or antigenic fractions thereof.

In this case, the diagnosis method of the invention can be either an ELISA assay, or a dipstick assay. In these assays of the invention, the heat- and optionally chemically-inactivated bacterial cells of the *Leptospira fainei* species are immobilized on a solid support. Said support is preferably a nitrocellulose membrane for the dipstick assay, or a microtiter plate for the ELISA assay. Alternative supports that can be used in these assays are well-known by the skilled person.

As used herein, the "ELISA assay of the invention" designates an ELISA (Enzyme-Linked Immunosorbent Assay) assay requiring the use of bacterial cells of the *Leptospira fainei* species that have been inactivated according to the inactivating method of the invention, or antigenic fractions thereof, said bacteria or fractions being immobilized on a solid support, preferably a microtiter plate. An ELISA assay according to the invention is disclosed in the experimental part of the application. ELISA assays are broadly used and well-described in the art.

As used herein, the "dipstick assay of the invention" designates a disptick assay requiring the use of bacterial cells of the *Leptospira fainei* species that have been inactivated according to the inactivating method of the invention, or antigenic fractions thereof, said bacteria or fractions being immobilized on a solid support, preferably a nitrocellulose membrane. A dipstick assay according to the invention is disclosed in the experimental part of the application. Dipstick assays are broadly used and well-described in the art.

Interestingly, in the present study, 11 out of 17 confirmed leptospirosis patients could be diagnosed earlier with the Dipstick assay of the invention than with the MAT (see Table 2 below). Similarly, in 16 out of 99 early sera from confirmed cases, the Dipstick assay of the invention was positive before the seroascension (10/37) or seroconversion (6/62) could be evidenced with the MAT. Therefore, the IgM dipstick assay of the invention presents an earlier positivity when compared to MAT in serial sera. Because an early diagnosis is of prime importance in the clinical management of leptospirosis, the possibility to ascertain the disease earlier in the course of the infection should be regarded as a real asset.

Immobilization of the bacteria (or fractions thereof) on the solid support is performed by conventional means which are well-known in the art. In case of a dipstick assay, the bacteria or fractions thereof can be for example sprayed on the solid support and let dry until total evaporation of the sprayed bacteria or fractions thereof. In case of an ELISA assay, the bacteria or antigenic fractions thereof can be put in contact with the surface of the solid support and let dry until total evaporation, for example during at least 6 hours at about 4° C., then the unbound bacteria (or fractions) are washed out by successive washings.

The solid support on which the bacteria (or antigenic fractions) are immobilized is then put in contact with the biological sample of the subject, in appropriate conditions so that the human immunoglobulins that are present in the said biological sample can bind to the immobilized bacteria (or fractions thereof). The said appropriate conditions (temperature, duration, etc.) depend on each kind of support, and it is routine matter to identify them for the bacteria (or fractions) of the invention. For example, few seconds (maximally one hour) are sufficient for the dipstick strip of the invention, while a few minutes (maximally twelve hours) are required for the ELISA assay of the invention.

The diagnostic method of the invention, and in particular the ELISA and dipstick assays of the invention, further comprises a step of detecting the human immunoglobulins bound to the immobilized antigen. This detection is typically performed with a revealing agent. This "revealing agent" can be an antibody or a functional fragment of same, either in the form of an immunoconjugate, or a labeled antibody in order to obtain a detectable and/or quantifiable signal.

In a preferred embodiment, said revealing agent is preferably an anti-human IgM antibody, more preferably an anti-human IgM antibody which is conjugated with a detectable label. Examples of detectable labels include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorot[pi]azinylamine fluorescein, dansyl chloride or phycoerythrin; example of luminescent material includes luminol, and examples of bioluminescent materials include luciferase, luciferin, and aequorin; examples of suitable radioactive material include $^{125}I$, $^{131}I$, $^{35}S$ or $^{3}H$.

It is also possible to use the antigen of the invention coupled with beads or nanoparticules. Coated beads or nanoparticles carrying the antigen of the invention would aggregate or immunocaptured in the presence of a subject's serum containing antibodies recognizing this antigen. This aggregation is easily detectable by conventional means, such as by microscopy, by flow cytometer, or naked eyes, etc.

The diagnostic assays of the invention advantageously contain a positive control to which the revealing agent binds without requiring the presence of the antigen-human immunoglobulin complexes. For example, if the revealing agent is anti-human IgM antibody, the positive control can consist in human IgM or at least the constant part thereof.

When the detection step reveals that the biological sample contains human immunoglobulins that are specific to the antigen of the invention, the said subject is diagnosed to have a *Leptospira* infection. It is then possible to administer an appropriate antibiotic treatment.

Antibiotic treatments that are currently used to prevent or fight against leptospirosis are well known to the skilled artisan. Such antibiotics include doxycycline, ceftriaxone, penicillin G and penicillin A. They are reviewed in Levett P. N. et al, Mandell, Douglas, and Bennett's Principales and Practice of Infectious Diseases, 2010.

Accordingly, in a second aspect, the present invention provides a method for identifying in vitro if a subject will benefit from the treatment with an antibiotic-containing composition, the method comprising:

a) conducting the diagnosis method of the invention on a biological sample of said subject, as defined above, using bacterial cells of a serovar of the *Leptospira fainei* species or an antigenic fraction of said bacterial cells, and
b) identifying if the subject will benefit from the treatment with an antibiotic-containing composition if the said biological sample contains human immunoglobulins that are specific to the said bacterial cells of the *Leptospira fainei* species, or to said antigenic fraction of said bacterial cells.

Preferably, the bacterial cells used in this method are bacterial cells of the *Leptospira fainei* species that have been inactivated according to the inactivating method of the invention described above.

Preferably, the bacterial cells used in this method belong to the *Leptospira fainei* serovar Hurstbridge.

More preferably, the bacterial cells used in this method are bacterial cells of the *Leptospira fainei* serovar Hurstbridge that have been inactivated according to the inactivating method of the invention.

As meant herein, a subject is "predicted to benefit from the treatment with an antibiotic-containing composition" if it is diagnosed to suffer from leptospirosis by the diagnosis method of the invention. This method is a very useful tool to avoid exposing antibiotics to subjects that do not suffer from leptospirosis, thereby preventing the emergence of bacterial resistance.

In another aspect, the present invention is drawn to an antibiotic-containing composition for use in treating a subject who has been diagnosed with leptospirosis using the method of the invention.

The present invention also relates to the use of an antibiotic for preparing a composition intended to treat a subject who has been diagnosed with leptospirosis using the diagnosis method of the invention.

Moreover, the present invention related to a method of treating a subject in need thereof, the method comprising administering an antibiotic-containing composition in subjects whose leptospirosis has been diagnosed using the diagnosis method of the invention.

In a second aspect, the present disclosure also provides kits useful for carrying out the diagnosis method described above.

The kits of the invention generally comprise a solid support coated with inactivated bacterial cells of the *Leptospira fainei* species, or antigenic fractions of said bacterial cells, and a revealing agent.

In a preferred embodiment, the said revealing agent is a labeled antibody, more preferably a labeled anti-human IgM antibody. Examples of detectable labels include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorot[pi]azinylamine fluorescein, dansyl chloride or phycoerythrin; example of luminescent material includes luminol, and examples of bioluminescent materials include luciferase, luciferin, and aequorin; examples of suitable radioactive material include $^{125}I$, $^{131}I$, $^{35}S$ or $^{3}H$.

In a preferred embodiment, the bacterial cells coated on the said solid support belong to the *Leptospira fainei* serovar Hurstbridge. In a more preferred embodiment, the said bacterial cells are bacterial cells of the *Leptospira fainei* serovar Hurstbridge that have been inactivated with the inactivating method of the invention.

In a preferred embodiment, the solid support of said kit is a microtiter plate or a nitrocellulose membrane.

In a preferred embodiment, the kit of the invention further comprises a control sample which is also recognized by said revealing agent. For example, if the revealing agent is an anti-human IgM antibody, the positive control can consist in human IgM or at least the constant part thereof.

The kits of the invention can also include instructions for interpreting the results obtained using the kit.

Kits may also comprise, e.g., a buffering agent, a preservative, or a protein stabilizing agent. The kits can further comprise components necessary for detecting the detectable label (e.g., an enzyme or a substrate). Each component of a kit can be enclosed within an individual container and all of the various containers can be within a single package, along with instructions for interpreting the results of the assays performed using the kit.

In another aspect, the present invention targets bacterial cells of the *Leptospira fainei* species, that have been inactivated with the inactivating method of the invention, or antigenic fractions of said bacterial cells. As mentioned previously, these bacterial cells or antigenic fractions thereof comprise at least one universal antigen that is recognized by a number of antibodies specific for *Leptospira* bacteria belonging to different serovars and/or serogroups.

Preferably, these bacterial cells belong to the *Leptospira fainei* serovar Hurstbridge.

In a preferred embodiment, said antigenic fraction is chosen from: liposaccharide, cytoplasmic proteins, secreted proteins, and envelop membrane proteins. It is more preferably liposaccharide (LPS).

In another aspect, the present invention is drawn to the use of:

i) bacterial cells of the *Leptospira fainei* species that have been inactivated with the inactivating method of the invention, or antigenic fractions of said bacterial cells, or ii) the kit of the invention, containing said bacterial cells and a revealing agent, in a diagnostic method for detecting leptospirosis infection in a subject in need thereof.

In a preferred embodiment, the said bacterial cells are bacterial cells of the *Leptospira fainei* serovar Hurstbridge, that have been preferably inactivated with the inactivating method of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

EXAMPLES

I. Material and Methods

1. Antigen Preparation

The antigen was prepared at Institut Pasteur, Unite de Biologie des Spirochetes, Paris, France. A 10 mL EMJH preculture of *Leptospira fainei* Hurstbridge BUT $6^T$ was used to inoculate one liter EMJH. This one-liter culture was incubated at 30° C. for 4-7 days with constant shaking until reaching an Optical Density greater or equal to 0.5 at 420 nm. The culture was then left standing at room temperature for 2-6 hours after addition of 2 mL of 37% (i.e. 0.2% v/v) of formaldehyde (or formalin). The formalin-killed culture was heated for 45 minutes in a boiling water bath. Lastly, the pH was adjusted to 9.6 and this preparation was stored at 4° C. This crude preparation was directly used as a fixed antigen in the RDTs (ELISA and dipsticks).

2. Development and Production of the ELISA Assay 2.1. Serum Samples

Blood samples from healthy volunteers with no history of leptospirosis and seronegative by MAT were collected from biobanque (Platform ICAReB/Investigation Clinique et Accès aux Ressources Biologiques, Institut Pasteur):

Serum samples negative and positive for leptospirosis were addressed to the National Reference Center of Leptospirosis (Institut Pasteur) for diagnostic purpose between 2010 and 2011 and originated from patients from mainland France and the French West Indies (Guadeloupe and Martinique).

The following groups were established based on the MAT (Microscopic Agglutination Test) which is the reference test for the serodiagnosis of leptospirosis so far (gold standard):

Group A (Negative controls): Two serologies for the same patient and whose results remained negative in MAT Group B (Positive cases): Two serologies for the same patient with a serocoversion or seroconversion at demonstrated (>=4-fold rise) in MAT with at least one pathogenic *Leptospira* serogroup and was therefore considered as a laboratory-confirmed leptospirosis case.

2.2. ELISA Protocol

Flat-bottom microtiter plates (Immulon 1B Thermo, Dutscher) were coated with 75 μL of the well-homogenized antigenic solution, overnight at 4° C. Alternatively the antigenic solution was left to evaporate at 37° C. for 1-3 days. The coated plates were then stored in a dry place at room temperature up to two years.

Plates were washed three times with PBS-0.2% Tween 20 (PBST), then incubated for 1 h at 37° C. (or overnight at 4° C.) with blocking solution, 75 μL PBS-Milk 5% (PBSM) (powders:Dutscher) pH 7.2. Plates were washed again three times with PBST. Duplicates of 75 μL dilution of the patient's sera in PBSM (1:400) were incubated for 1 h at 37° C. One dilution range of a pool of positive serum samples (1:400 to 1:204 800) and one negative control were included on each plate as internal standards. This pool was constituted by 50 positive serum samples exhibiting MAT reciprocal titers 800 with at least one pathogenic *Leptospira* serogroup.

The plates were washed three times with PBST. 75 μL of rabbit anti-human IgM-peroxidase conjugate (Biorad) diluted at 1:500 in PBSM were added to each well and plates were incubated for 1 h at 37° C.

Plates were washed five times with PBST. 75 μL of substrate buffer (0.5 mM 2-2'-azino di-ethyl benz-thiazoline-6-sulphonic acid (ABTS) (Roche), were added to each well. Plates were read at 415 nm with ELISA reader (Biorad) after 30 min of incubation in the dark at 37° C.

The end-point cut-off was established by titration as the mean OD 405 value of the 20 serum samples negative for leptospirosis plus 3 standard deviations.

2.3. Results of the ELISA Protocol

A total of 449 sera were analyzed:

| Technique | MAT | ELISA IgM |
|---|---|---|
| negative | 308 (TN) | 304 |
| positive | 141 (TP) | 135 |

TN = Truth Negative = 308
TP = Truth Positive = 141
FP = False-Positive = 4
FN = False-Negative = 6

Sensitivity:

TP/(TP+FN)×100=141/(141+6)×100=96%

Specificity:

TN/(TN+FP)×100=308/(308+4)=99%

Positive Predictive Value (VPP):

TP/(TP+FP)×100=141/(141+4)×100=97%

Negative Predictive Value (VPN):

TN/(TN+FN)×100=308/(308+6)×100=98%

Precocity of the Test:

| n = 282(141patients) | MAT−/Elisa− | MAT−/Elisa+ | MAT+/Elisa− | MAT+/Elisa+ |
|---|---|---|---|---|
| first serologies | n = 80 (57%) | n = 60 (42.5%) | n = 1 (0.5%) | n = 0 |
| second serologies | n = 0 | n = 0 | n = 6 (4.3%) | n = 135 (95.7%) |

In more than half of the cases (57%), the ELISA assay of the invention was positive on the first serum, whereas the MAT was negative.

3. Development and Production of the Dipstick Assay 3.1. Serum Samples

Leptospirosis cases were defined as confirmed when a clinical and epidemiological suspicion was complemented by either a positive specific PCR evidencing genomes of pathogenic *Leptospira* sp. in the blood or urine of the patient or when two serological analyses using the reference MAT on acute and convalescent sera showed a seroconversion (from nil to a reciprocal titer 400) or a significant seroascencion (at least a fourfold raise in reciprocal titers), according to the WHO recommended standards. Probable cases were defined as clinical and epidemiological suspicion together with a unique serum with a MAT reciprocal titer greater than 400 [Berlioz-arthaud A. et al, *Trans R. Soc. Trop. Med. Hyg.* 2007]. The panel of strains used for MAT was adapted to the local epidemiology.

All sera used in this study were addressed to Institut Pasteur for diagnostic purpose and originated from patients from New Caledonia, mainland France and the French West Indies (Martinique and Guadeloupe). They were stored at −20° C., selected according to case definitions, then tested blindly. To assess the sensitivity of the dipstick assay, only MAT positive sera from confirmed cases were used. The specificity was assessed using MAT negative healthy or pathological sera from the reference laboratories of the Institut Pasteur in Nouméa (IPNC) or Paris.

The IPNC and the NRC are reference diagnostic laboratories for leptospirosis. In New Caledonia, leptospirosis is a notifiable disease. The serum samples used in this study were selected from the IPNC and NRC collections of sera issued from routine diagnostic activities and as part of public health surveillance. This biobank of sera was declared to the French Ministry of Research (DC-2010-1222, Collections number 1 and 2). This study was part of a protocol approved by the Institut Pasteur (protocol # RBM2008-16) and the French Minister for Education & Research (protocol # AC-2007-44). All sera were tested as anonymous samples.

3.2. Dipstick Protocol

The positive control line was made of purified human IgM (MP Biomedicals) at 2 mg/mL. Both control and test lines were sprayed as lines onto nitrocellulose membranes. The crude formalin-treated bacteria preparation was directly used as a fixed antigen for the test line. Gold particles labelled with goat anti-human IgM (BBI International BA.GAHM40/X) was used as the capture mobile phase to construct our one-step vertical flow immunochromatography dipsticks, as described before [Chanteau S. et al, *PLoS Med*, 2006].

Preliminary experiments determined a 1/400 dilution of sera in Phosphate Buffer Saline (PBS, pH 7.4) as suitable. Briefly, strips were introduced into 200 μL diluted serum in 5 mL polystyrene tubes, for 15 minutes. The strips were then removed and placed on absorbent kitchen paper and read within 5 minutes. All results were recorded using a grading scale from 0 (no visible trace on test band) to 3+(intensity of the test band equal to the intensity of the control band). The grading included a "weak" value for low but visible traces on the test band. Weaks, 1+, 2+ and 3+ were then considered positive for further analysis and 0 was considered as negative. All the strips were archived for further checking.

All analyses were run blindly: any person involved in one particular analysis had no access to the results of the other tests results from the same serum. The sensitivity was evaluated using 187 confirmed leptospirosis cases sera with a MAT reciprocal titer 400. The specificity was assessed using 221 negative sera (142 from New Caledonia, 79 from mainland France): 12 anti-Chikungunya virus IgM positive sera, 58 anti-dengue virus IgM positive sera from all 4 serotypes, 6 anti-hepatitis A virus total Ig positive sera, 7 rheumatoid factor positive sera, 25 syphilis (TPHA and VDRL) positive sera, one acute malaria serum and 112 sera from healthy blood donors. All these 221 negative control sera have been tested using MAT and were all negative (titer <100).

Possible false negative result due to high level of anti-Leptospira IgM (zone phenomenon) was controlled using two positive sera with 25,600 and 51,200 MAT titers, respectively.

3.3. Stability Assays

The strips were stored at 4° C. in sealed aluminium foils, and the test was performed at laboratory room temperature (20°-23° C.).

The predictive shelf life of the coated-strips was assessed by testing serial dilutions of a MAT positive serum (MAT reciprocal titer=800, pointing to serogroup Icterohaemorrhagiae) twice per week over a period of 3 weeks exposure of the strips at 60° C. During this period, the positive control serum was kept at 4° C. to avoid repeated freeze-thaw cycles. This accelerated stability method is equivalent to two years of actual storage time at 25° C. [Banoo et al, *Nat. Rev. Microbiol.* 2010].

3.4. Reproducibility and Repeatability

Several experiments were performed to evaluate the robustness of the dipstick assay (reproducibility and repeatability):
  Simulation of tropical fields conditions by performing the tests in parallel at laboratory room temperature and at 37° C. in an incubator;
  blind testing of a panel of four sera (3 positives and one negative) by three different operators on three different days;
  blind testing of one same serum 14 times using two different batches of strips by the same operator.
  blind reading of strips results by two technicians on 117 sera (28 negative and 89 positive samples), and by three technicians on 97 sera (16 negative and 81 positive samples).

3.5. Comparative Kinetics of MAT and the Dipstick Assay of the Invention

The earliness of IgM seroconversion using MAT or the dipstick assay of the invention was assessed on serial sera (day 2 to day 18 after the onset of symptoms) from 17 confirmed cases, based on the date of onset as declared by the patients.

The dipstick assay was also used on early sera from 99 PCR positive confirmed patients but still MAT negative (reciprocal titers=0, 100 or 200).

150 MAT positive sera from probable cases, including 124 sera from the IPNC collection, and 26 from the French National Reference Centre, were tested using this dipstick assay.

3.6. Comparison with 3 Commercial Diagnostic Assays

To compare the newly developed RDT with currently available techniques, the performance of these assays was compared on identical sera from New Caledonia. To assess the sensitivity, 72 MAT-positive sera from confirmed cases were randomly selected from the 118 New Caledonian control sera. For the specificity, 72 negative controls were randomly-selected, corresponding to 10 anti-Chikungunya virus IgM positive sera, 30 healthy blood donors, 11 anti-dengue virus IgM positive sera from all 4 serotypes, 6 anti-hepatitis A virus total Ig positive sera, 7 rheumatoid factor positive sera, 7 syphilis (TPHA and VDRL) positive sera, one acute malaria serum. The results using the dipstick assay of the invention were compared with those obtained using two Elisa assays (*Leptospira* IgM ELISA, Panbio, Inverness Medical, QLD Australia, and SERION ELISA classic *Leptospira* IgG/IgM, Institut Virion/Serion GmbH, Germany) and one lateral flow IgM immunochromatography assay (Leptocheck, Zephyr Biomedicals, India). The Serion ELISA test was used together with the Rheumatoid Factor Absorbent as recommended by the manufacturer. All tests were made within a 5 day period. For calculations, the "uncertain" results of ELISA were considered as positive.

3.7. Statistical Analysis

The evaluation of the dipstick assay of the invention for the serodiagnosis of leptospirosis was performed according to the WHO Tropical Diseases Research Diagnostics Evaluation Expert Panel for the evaluation of diagnostic tests for infectious diseases [Banoo et al, *Nat. Rev. Microbiol.* 2010].

Sensitivity (Se), specificity (Sp), positive and negative predictive values (PPV and NPV, respectively) of the dipstick assay were calculated, using the reference MAT serology as the gold standard. Both tests were conducted at the IPNC. The 95% confidence intervals (95% CI) were calculated using the Wilson method.

The likelihood ratios (LR) were also calculated. The positive LR (LR+=Se/[1−Sp]) indicates how many times a positive result is more likely to be observed in specimens with the target disorder than in those without the target disorder. The negative LR (LR−=[1−Se]/Sp) indicates how many times a negative result is more likely to be observed in specimens with the target disorder than in those without the target disorder. The test is more accurate the more LR differs from 1. LR+ above 10 and LR− below 0.1 were considered convincing diagnostic evidence [Jaeschke R et al, *JAMA* 1994]. The 95% CIs were calculated for LR+ and LR− [Simel D L. *J. CLin. Epidemiol.* 1991].

The diagnostic odds ratio (DOR) measures of test performance by combining the strengths of sensitivity and specificity, with the advantage of accuracy as a single indicator. These characteristics lend the DOR particularly useful for comparing tests whenever the balance between false negative and false positive rates is not of immediate importance [Glas A S. et al, *J. Clin. Epidemiol.* 2003]. The DOR is defined as the ratio of the odds of positive test results in specimens with the target disorder relative to the odds of positive test results in specimens without the target disorder. It was calculated as follows:

$$DOR=(Se/[1-Se])/([1-Sp]/Sp)$$

The DOR does not depend on prevalence and its value ranges from 0 to infinity, with higher values indicating better discriminatory test performance. The 95% CIs for DOR values were calculated [Armitage P. et al, *Statistical methods in medical research*, 1994].

3.8. Results of the disptick assay of the invention a) Specificity and Sensitivity Out of the 187 gold standard positive sera tested, 168 had a positive dipstick result. The putative serogroups of the 19 dipstick negative sera were: Icterohaemorrhagiae (n=12), Pyrogenes (n=3), Australis (n=2), Panama (n=1) and one could not be determined due to co-agglutination of multiple serogroups.

Out of the 221 MAT negative sera tested, 207 were had a negative dipstick result. All 14 dipstick positive sera were graded "weak" and originated from 9 healthy blood donors and five patients positive for anti-dengue virus IgM.

The sensitivity and specificity of the dipstick assay of the invention were therefore, respectively, Se=89.8% [95% CI, 84.7-93.4] and Sp=93.7% [95% CI, 89.65-96.2]. The Likelihood Ratios (LR) were therefore LR+=14.18 [95% CI, 8.52-23.56] and LR−=0.11 [95%; 0.01-0.17]; and the Diagnostic Odds Ratio DOR of 130.74 [95% CI, 63.65-268.52].

Figure 1:
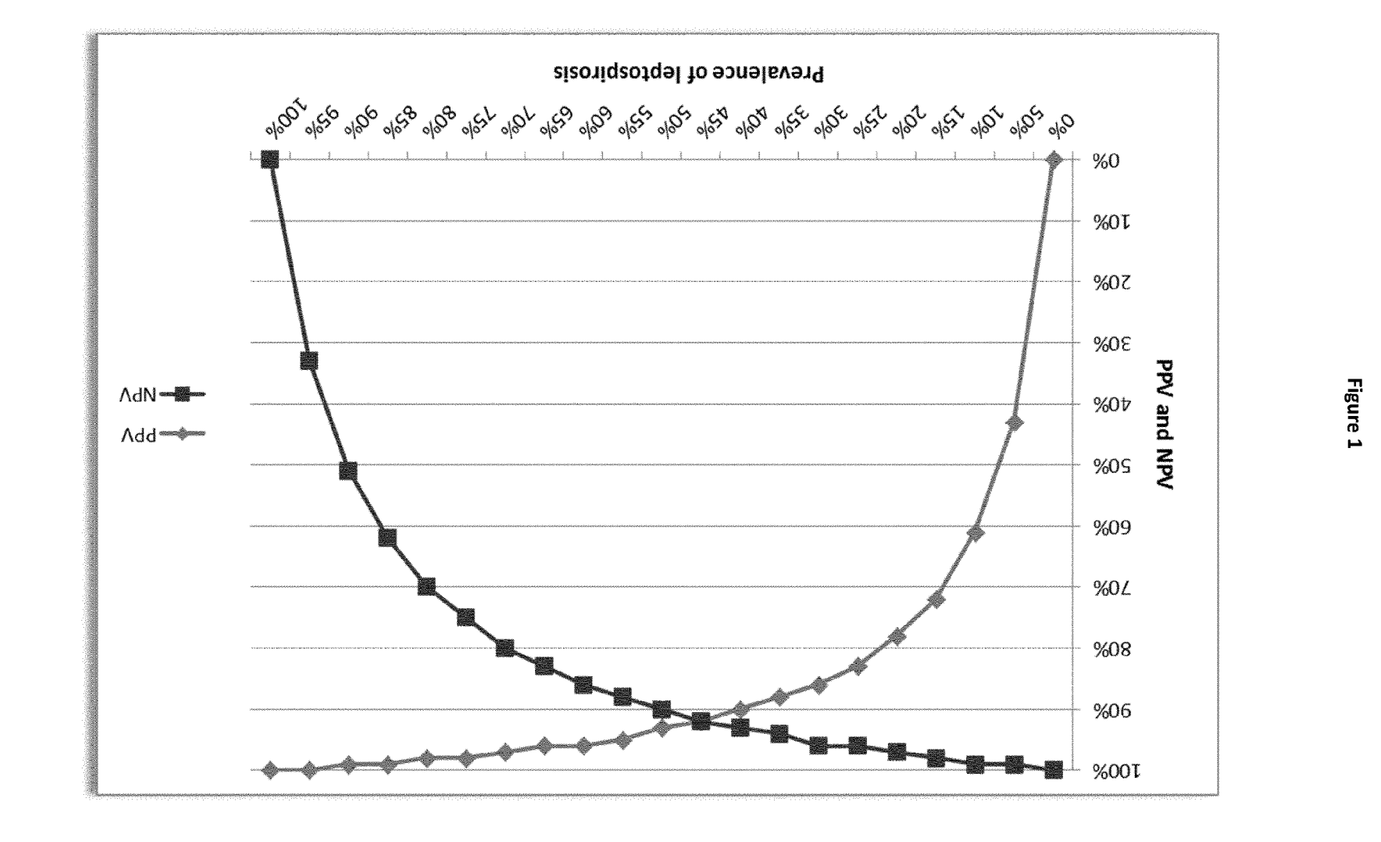
FIG. 1 discloses the Positive and Negative Predictive Values (PPV, NPV) for the diagnosis of leptospirosis using the IgM dipstick of the invention, using 187 positive and 221 negative serum specimens.

The positive and negative predictive values according to prevalence are presented in FIG. 1.

The absence of false negative due to zone phenomenon was demonstrated using two positive sera with very high MAT reciprocal titers (25,600 and 51,200) serially two-fold diluted (1/400 to 1/6,400).

b) Temperature Stability and Accelerated Aging Method for Shelf Life

The dipstick results of 10 MAT positive sera run at 37° C. were identical to those run at 25° C.

Serial two-fold dilutions (from 1/400 to 1/12,800) of one MAT positive serum (titer 800) where tested twice a week for three weeks with dipstick exposed at 60° C. At day 1, the dipstick reciprocal titer was 6,400, and remained the same till day 17. At day 21, the reciprocal titer decreased to 3,200 (one dilution of the serum).

c) Reproducibility and Repeatability

One serum tested 14 times with strips from the two different batches gave 14 similar results, including the grade.

Inter-readers variability was assessed by two independent operators on 177 sera (28 negative and 149 positive) of which 157 sera were read by three independent operators. These readings provided an excellent inter-operator agreement in all cases (>99%) but one weakly positive dipstick from a probable case was rated "weak" by two operators but negative by the third one.

Inter-operator variability was also assessed using 4 sera (dipstick graded from negative to 3+) blindly and independently tested at three different days by three different operators. Two operators provided perfectly concordant grading results on all three tests, the third one graded "weak" a negative serum once out of the three tests.

d) Comparative Kinetics of MAT and RDT

Of 17 confirmed cases analysed (see Table 2):
one patient (number 1) seroconverted for MAT at day 6 (pointing to Icterohaemorrhagiae) but remained negative for the dipstick assay.
oppositely, 5 PCR confirmed patients (numbers 2-6) were MAT negative whereas they were positive for the dipstick assay. For one of these patients (number 6), PCR and dipstick assays were both positive at day 4 after onset of symptoms.
five patients (numbers 7-11) were positive for MAT and the dipstick assay on the same day (days 5-11 after the onset of symptoms);
lastly, for 6 patients (numbers 12-17), the dipstick assay was positive earlier than the MAT (day 3 to day 7). Out of these 6, four (numbers 12, 15, 16 and 17) had a positive blood PCR and dipstick results on the same day (on days 5, 4, 7 and 3 respectively).

Similarly, in 16 out of 99 early sera from confirmed patients from New Caledonia, the dipstick assay was positive whereas the MAT was still negative (6 out of 62) or displayed low titers (titer 100 for 4 out of 21; titer 200 for 6 out of 16).

Of 150 sera from probable cases of leptospirosis (unique sera with a MAT 400), 109 gave a positive result using the dipstick assay of the invention, corresponding to a concordance of 72.7% [65-79.1].

Out of these, 108 had a MAT>400, from which 81 (75% [66.1-82.2]) were positive for the dipstick assay of the invention, while 63 had a MAT titer >800, from which 53 (84.1% [73.2-91.1]) were positive for the dipstick assay of the invention.

The use of 72 Gold Standard positive (MAT≥400 from confirmed cases) and 72 negative (MAT<100) serum specimens selected randomly allowed a comparison of the dipstick assay of the invention with three commercially available tests: two ELISA tests and one IgM lateral flow immunochromatographic assay.

The results of these tests are detailed in Table 3.

TABLE 3

| MAT | Dipstick 1/400 e | Leptocheck | Elisa Serion (+RF absorbant) | Elisa Panbio |
|---|---|---|---|---|
| | Positive 59 | Positive 59 | Positive 58 | Positive 53 |
| | | | Negative 1 | Negative 5 |
| | | | | Positive 0 |
| | | | | Negative 1 |
| | | | Positive 0 | Positive 0 |
| | | Negative 0 | | Negative 0 |

TABLE 2

| Patient | Leptospirosis diagnosis | Putative serogroup | Sera tested * | MAT positive* | RDT positive* |
|---|---|---|---|---|---|
| 1 | blood PCR+ at D4 | Icterohaemorrhagiae | D4-6 | D6 | — |
| 2 | blood PCR+ at D8 | Icterohaemorrhagiae | D8-9; D11-14 | — | D9 |
| 3 | blood PCR+ at D2 | Icterohaemorrhagiae | D2-6 | — | D5 |
| 4 | blood PCR+ at D4 | Icterohaemorrhagiae | D4; D6-12 | — | D6 |
| 5 | blood PCR+ at D1 | Pyrogenes | D1-2; D4-5; D7 | — | D7 |
| 6 | blood PCR+ at D4 | Ballum | D4-6 | — | D4 |
| 7 | blood PCR+ at D6 | Icterohaemorrhagiae | D6-8; D11 | D11 | |
| 8 | blood PCR+ at D4 | Icterohaemorrhagiae | D4-8 | D7 | |
| 9 | Seroconversion D4-D7 | Icterohaemorrhagiae | D4; D7; D9 | D7 | |
| 10 | urine PCR+ at D5 | Icterohaemorrhagiae | D5-6 | D5 | |
| 11 | Seroascension D5-D9 | Icterohaemorrhagiae | D6, D9, D11 | D6 | |
| 12 | blood PCR+ at D5 | Icterohaemorrhagiae | D5-8; D10; D12-13 | D13 | D5 |
| 13 | urine PCR+ at D8 | Icterohaemorrhagiae | D7-12; D17 | D17 | D7 |
| 14 | blood PCR+ at D3 | Icterohaemorrhagiae | D3-6 | D6 | D5 |
| 15 | blood PCR+ at D4 | Icterohaemorrhagiae | D3-7; D9-12 | D5 | D4 |
| 16 | blood PCR+ at D7 | Icterohaemorrhagiae | D7-11; D13-17 | D17 | D7 |
| 17 | blood PCR+ at D3 | Icterohaemorrhagiae | D3-6 | D6 | D3 |

TABLE 3-continued

| MAT | Dipstick 1/400 e | Leptocheck | Elisa Serion (+RF absorbant) | Elisa Panbio |
|---|---|---|---|---|
| Positive 72 | | | Negative 0 | Positive 0 |
| | | | | Negative 0 |
| | | | Positive 8 | Positive 1 |
| | | Positive 11 | | Negative 7 |
| | | | Negative 3 | Positive 0 |
| | Negative 13 | | | Negative 3 |
| | | | Positive 0 | Positive 0 |
| | | Negative 2 | | Negative 0 |
| | | | Negative 2 | Positive 0 |
| | | | | Negative 2 |
| Sensitivity | 81.9% | 97.2% | 91.7% | 75% |
| | [71.5-89.1] | [90.4-99.2] | [83-86.1] | [63.9-83.6] |
| Negative 72 | Negative 69 | Negative 38 | Negative 59 | Negative 72 |
| Specificity | 95.8% | 52.8% | 81.9% | 100% |
| | [88.4-98.6] | [41.4-63.9] | [71.5-89.1] | [94.9-100] |
| LR+ | 19.7 [6.5-59.9] | 2.1 [1.6-2.6] | 5.1 [3.1-8.3] | NA |
| LR- | 0.2 [0.1-0.3] | 0.05 [0.01-0.21] | 0.1 [0.05-0.2] | 0.25 [0.17-0.37] |
| DOR | 104.4 [28.4-384] | 39.1 [8.9-171.8] | 49.9 [17.8-139.7] | NA |

NA: Not Applicable
\* LR+: Positive Likelihood Ratio—[95% CI]
† LR−: Negative Likelihood Ratio—[95% CI]
‡ DOR: Diagnostic Odds Ratio—[95% CI]

Sensitivity (%), number of positive rapid diagnostic test among patients with serological evidence (MAT) of leptospirosis (n=72)–[95% CI].

Specificity (%), negative rapid diagnostic test among serum samples from patients with no serological evidence (MAT) of leptospirosis (n=72)–[95% CI].

The IgM ELISA from Panbio had 100% specificity on these specimens together with the lowest sensitivity (75%). This 100% specificity does not allow the calculation of a Diagnostic Odds Ratio (DOR) that would however be very high. The ELISA test from Serion had both a good sensitivity (91.7%) and a good specificity (81.9%), therefore showing a good DOR of 49.9. Another rapid diagnostic test, namely Leptocheck (from Zephyr) had a very good sensitivity (91.2%) but a quite low specificity (52.8%), giving a DOR of 39.1. The Dipstick assay of the invention displayed a very good specificity (95.8%) and a good sensitivity (81.9%) and had therefore a very good DOR of 104.4. The corresponding curves of predictive values according to the prevalence of the two IgM rapid tests on these specimens are compared in the FIG. 2.

Figure 2:
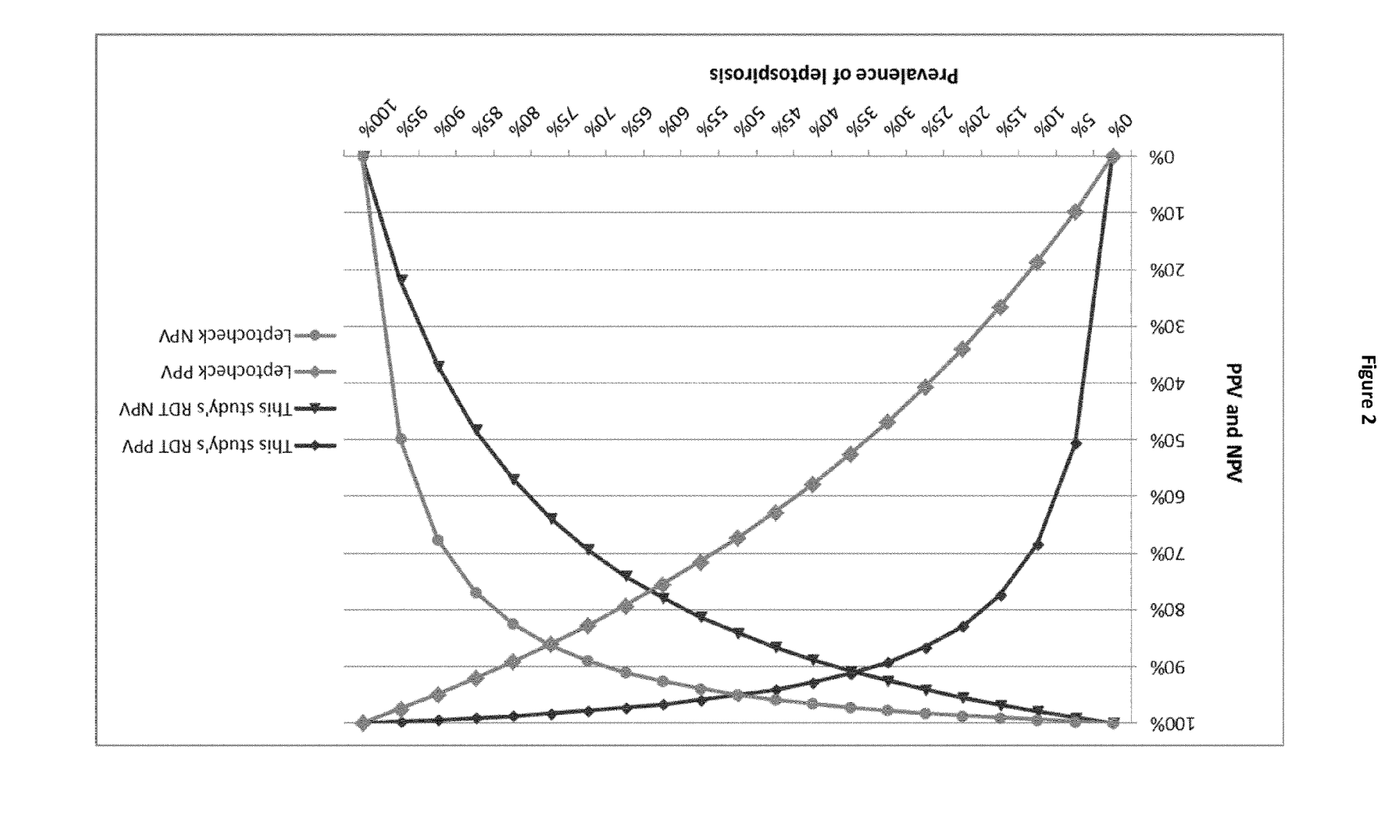
FIG. 2 discloses comparative Positive and Negative Predictive values (PPV, NPV) for the diagnosis of leptospirosis using the IgM dipstick of the invention and a commercial lateral flow IgM assay. This comparison was conducted on 72 positive and 72 negative serum specimens randomly selected from New Caledonian specimens.

When considering the need of RDT for bedside diagnosis, the comparison of the Dipstick assay of the invention with assays that are commercially available shows that the dipstick assay of the invention has a lower sensitivity (81.9% versus 97.2%) but a much higher specificity (95.8% versus 52.8%) and therefore a better Diagnostic Odds Ratio (104.4 versus 39.1). This better performance is also shown by the comparison of the curves of their predictive values according to prevalence (FIG. 2).

Importantly, only sera from confirmed leptospirosis cases were used for this evaluation. Therefore, the positive samples for the evaluation of sensitivity were both Gold Standard positive (a MAT reciprocal titer of at least 400) and from confirmed leptospirosis cases (either a positive PCR or a seroconversion from nil to ≥400 or a ≥4-fold rise in MAT reciprocal titers in paired sera). Additionally, all negative sera for specificity evaluation were tested blindly using the reference MAT and were only considered as true negatives if the MAT reciprocal titer was below 100. These latter originated from both healthy volunteers and a selection of patients with pathologic conditions of relevance in endemic countries. Using this clearly defined case definition, the sensitivity and specificity of the dipstick assay of the invention were 89.8% and 93.7% respectively. These results compare and are slightly better than the ones reported by Smits et al. who reported a 85.8% sensitivity and a 93.6% specificity with another Dip Stick assay (Smits H L. Clin. Diagn. Lab. Immunol. 2001). To increase the statistical power of this evaluation, were included serum samples as old as 3 years and 3 months from New Caledonia, stored frozen at −20° C. It is well recognized that the long term storage of serum specimens at −20° C. and their freeze/thawings may result in a drop of IgM titers. Actually, the sensitivity was higher in sera stored for less than two years than in sera stored for more than two years (90.6% versus 81.5%). This may have resulted in a slight under-estimation of the sensitivity of the Dipstick assay of the invention.

Importantly, the dipstick assay of the invention reacts with antibodies to at least serogroups Australis, Autumnalis, Ballum, Bataviae, Canicola, Cynopteri, Grippotyphosa, Hebdomadis, Icterohaemorrhagiae, Panama, Pomona, Pyrogenes, Sejroe and Tarassovi, indicating that the assay reacts broadly with antibodies mounted against *Leptospira* strains circulating worldwide.

These results demonstrate that the diagnostic test of the invention is useful in endemic contexts, especially in low and middle-income countries. Actually, most of the leptospirosis burden occurs in the back-country with delayed access to the reference laboratory. In epidemics situations, especially during post-disaster periods like in the Philippines in 2009, reference diagnostic tests are seldom if ever available. Therefore, a diagnosis test with good diagnostic performances would also be particularly useful. The use of the dipstick assay of the invention as an initial screen for leptospiral infections would allow facilitating the difficult differential diagnosis of leptospirosis.

The invention claimed is:

1. An in vitro method for diagnosing a *Leptospira* infection in a biological sample of a subject, comprising:
   providing a biological sample of a subject;
   contacting said sample with heat and chemical inactivated bacterial cells of *Leptospira fainei* serovar Hurstbridge, or an antigenic fraction of said heat and chemical inactivated bacterial cells, wherein said heat and chemical inactivated bacterial cells or antigenic fraction thereof are immobilized on a solid support; and
   assaying for binding of antibodies in said biological sample with said heat inactivated bacterial cells or antigenic fraction thereof immobilized on said solid support;
   wherein said heat and chemical inactivated bacterial cells or antigenic fraction thereof immobilized on said solid support react with antibodies against *Leptospira* serogroups Australis, Autumnalis, Ballum, Bataviae, Canicola, Cynopteri, Grippotyphosa, Hebdomadis, Icterohaemorrhagiae, Panama, Pomona, Pyrogenes, Sejroe, and Tarassovi.

2. The method of claim 1, wherein binding of antibodies in said biological sample with said heat and chemical inactivated bacterial cells or antigenic fraction thereof immobilized on said solid support is detected.

3. The method of claim 1, wherein binding of antibodies in said biological sample with said heat and chemical inactivated bacterial cells or antigenic fraction thereof immobilized on said solid support is not detected.

4. The method of claim 1, wherein said antigenic fraction is selected from lipopolysaccharide (LPS), cytoplasmic proteins, secreted proteins, and envelope membrane proteins.

5. The method of claim 4, wherein said antigenic fraction is LPS.

6. The method of claim 1, wherein said leptospirosis infection is due to bacteria belonging to at least one serogroup selected from the group consisting of: serogroup Australis, Autumnalis, Ballum, Bataviae, Canicola, Cynopteri, Grippotyphosa, Hebdomadis, Icterohaemorrhagiae, Panama, Pomona, Pyrogenes, Sejroe, and Tarassovi.

7. The method of claim 1, wherein the method is an ELISA assay.

8. The method of claim 1, wherein the method is a dipstick assay.

* * * * *

UNITED STATES PATENT AND TRADEMARK OFFICE
CERTIFICATE OF CORRECTION

PATENT NO. : 9,714,944 B2  
APPLICATION NO. : 14/433030  
DATED : July 25, 2017  
INVENTOR(S) : Pascale Bourhy et al.

It is certified that error appears in the above-identified patent and that said Letters Patent is hereby corrected as shown below:

On the Title Page

In the Inventors, "Faradibano Nato" should read --Faridabano Nato--

Signed and Sealed this  
Thirty-first Day of October, 2017

Joseph Matal  
*Performing the Functions and Duties of the*  
*Under Secretary of Commerce for Intellectual Property and*  
*Director of the United States Patent and Trademark Office*